United States Patent [19]

Pouvreau

[11] Patent Number: 5,797,970
[45] Date of Patent: Aug. 25, 1998

[54] SYSTEM, ADAPTOR AND METHOD TO PROVIDE MEDICAL ELECTRICAL STIMULATION

[75] Inventor: Yves Pouvreau, Le Rheu, France

[73] Assignee: Medtronic, Inc., Minneapolis, Minn.

[21] Appl. No.: 708,381

[22] Filed: Sep. 4, 1996

[51] Int. Cl.$^6$ ............................................. A61N 1/362
[52] U.S. Cl. ............................................. 607/9; 607/116
[58] Field of Search ........................ 607/4, 9, 27, 28, 607/29, 34, 37, 116, 122, 123

[56] References Cited

U.S. PATENT DOCUMENTS

| | | | |
|---|---|---|---|
| 3,625,201 | 12/1971 | Murphy, Jr. | 607/27 |
| 3,800,801 | 4/1974 | Gaillard. | |
| 4,114,628 | 9/1978 | Rizk | 607/4 |
| 4,289,134 | 9/1981 | Berstein | 607/9 |
| 4,628,934 | 12/1986 | Pohndorf et al. | 607/251 |
| 4,679,572 | 7/1987 | Baker, Jr. | |
| 4,741,342 | 5/1988 | Scotts. | |
| 4,932,407 | 6/1990 | Williams. | |
| 5,170,802 | 12/1992 | Mehra. | |
| 5,224,491 | 7/1993 | Mehra. | |
| 5,304,139 | 4/1994 | Adams et al. | |
| 5,325,870 | 7/1994 | Kroll et al. | 607/122 |
| 5,336,253 | 8/1994 | Gordon et al. | 607/122 |
| 5,387,233 | 2/1995 | Alferness et al. | |
| 5,476,498 | 12/1995 | Ayers. | |
| 5,514,161 | 5/1996 | Limousin. | |
| 5,531,781 | 7/1996 | Alferness et al. | |

OTHER PUBLICATIONS

Daubert et al. "Atrial Tachyarrhythmias Associated with High Degree Interatrial Conduction Block: Prevention by Permanent Atrial Resynchronisation"–EUR.J.C.P.E. Apr. 1994 1:35–44.

Daubert et al. "Renewal of Permanent Left Atrial Pacing Via The Coronary Sinus"Cardiostim 92 EUR.J.C.P.E., vol. 2, No. 2, Jun. 1992 (Suppl.1A) #298.

Daubert et al. "Biatrial Synchrononous Pacing to Optimize the Hemodynamic Benefit of DDD Pacing in Hypertrophic Obstructive Cardiomyopathy (HOCM)"—Circulation vol. 92(8) supplement I: I–780–I–781, Oct. 15, 1995.

(List continued on next page.)

*Primary Examiner*—William E. Kamm
*Attorney, Agent, or Firm*—Michael J. Jaro; Harold Patton

[57] ABSTRACT

A system for providing medical electrical stimulation, the system features a pulse generator, the pulse generator generating electrical stimulation pulses of a first amplitude and a second amplitude, first and second elongated leads coupled to the pulse generator, a zener diode which directs electrical stimulation pulses of a first amplitude to the first lead and directs electrical stimulation pulses of a second amplitude to the first lead and the second lead, the means for directing electrical stimulation pulses coupled to the pulse generator. In the preferred embodiment the diode is electrically coupled to one of the leads such that electrical stimulation of a first amplitude is not passed through the diode while electrical stimulation of a second amplitude is passed through the diode. Overall the adaptor permits a single channel of stimulation to be split and provided to two areas of the heart merely be adjusting the amplitude of the stimulation pulses.

7 Claims, 5 Drawing Sheets

OTHER PUBLICATIONS

Daubert et al, "Biatrial Synchronous Pacing: A New Approach for Prevention of Drug Refractory Atrial Flutter"—Clinical Cardiology: Hilton CA Abstract 2539.

Daubert et al, "3 Years Experience of Permanent Atrial Resynchronization for Preventing Arrhythmias and Hemodynamic Disorders Related to Major Interatrial Blocks"—190 1812 European Hart Journal 13(abstr.Suppl.) 326 Aug. 1992.

Daubert et al, "Renewal of Permanent Left Atrial Pacing Via the Coronary Sinus"—NASPE Abstract, Apr. 1992, Part II, PACE, vol. 15.- #255.

Stokes et al, "All Impedances Are Not Created Equal: Efficiency vs. Expediency–or–Everything You Need To Know About Impedance To Design The Optimum Lead"—Medtronic S&T Journal Oct. 1994.

Daubert et al. "Resynchronisation atriale permanente par la stimulation biatriale synchrone pour le tratement preventif du flutter auriculaire associe a un bloc interauriculaire de haut degre"—Arch Mal Cover 87 (suppl. 11):1535–46 Nov. 1994.

SYSTEM, ADAPTOR AND METHOD TO PROVIDE MEDICAL ELECTRICAL STIMULATION

FIELD OF THE INVENTION

The present invention generally relates to medical electrical stimulation, and more particularly, to a system and method to provide medical electrical stimulation to either a single chamber on one side of the heart or two chambers on each side of the heart, for example, either an atrium or both atria of a heart.

BACKGROUND OF THE INVENTION

Electrical stimulation of body tissue and organs is often used as a method of treating various pathological conditions. Such stimulation generally entails making an electrical contact between body tissue and an electrical pulse generator through use of one or more stimulation leads. Various lead structures and various techniques for implanting these lead structures into body tissue and particularly the heart have been developed.

For example, a transvenous endocardial lead establishes electrical contact between an electrical pulse generator and heart through placement of a lead in the venous system. Specifically, a transvenous endocardial lead is passed through a vein, with the assistance of a fluoroscope, into the heart where it may be held in contact with the endocardium by the trabeculae of the heart chamber, such as the ventricle.

There are, however, disadvantages to transvenous leads including: possible damage to the vein, such as perforation or laceration during insertion; possible failure to securely attach and maintain electrical contact with the heart; possible perforation of the heart wall by the lead; and because direct visual inspection of the lead placement is not possible, possible improper lead placement in the heart. In addition, the usage of a fluoroscope to visualize lead position carries its own set of risks to both the patient as well as to the physician.

Besides these disadvantages there are additional situations in which the installation of a transvenous endocardial pacing lead is either not feasible or not recommended. These situations include the case when the area to be stimulated is the left side of the heart.

The left side of the heart is presently not available for the implantation of chronic or long term transvenous leads due to risk of thrombus or clot formation. In particular, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the heart. For example, in patients with dilated cardiomyopathy, electrical stimulation of both the right side and the left side of the heart has been shown to be of major importance to improve the patient's well-being and manage heart failure. See, for example, Cazeau et al., "Four Chamber Pacing in Dilated Cardiomyopathy," PACE, November 1994, pgs. 1974–79. See also Brecker and Fontainem, St. et al., "Effects Of Dual Chamber Pacing With Short Atrioventricular Delay In Dilated Cardiomyopathy," Lancet November 1992 Vol 340 p 1308–1312; Xiao HB et al., "Effect Of Left Bundle Branch Block On Diastolic Function In Dilated Cardiomyopathy," Br. Heart J 1991, 66(6) p 443–447; and Fontaine G et al, "Electrophysiology Of Pseudofunction," Cl. Meere (ed) Cardiac pacing, state of the art 1979, Pacesymp, 1979 Montreal.

Typically, multi chamber pacing has been accomplished by using a conventional pulse generator in which more than two leads have been coupled. The coupling of three or more leads has been accomplished using an adaptor or connector. One connector which has permitted atrial leads to be coupled to the heart has been developed by Medtronic. This connector, the SP 2872 coupled two leads together in parallel. Such a connector, however, provides this bi-atrial stimulation at all times. Thus, it is not possible to only stimulate one atrium. Stimulation of only one atrium, however, is at times desirable.

An improvement in the field was seen in Limousin U.S. Pat. No. 5,514,161 entitled "Methods And Apparatus For Controlling Atrial Stimulation In A Double Atrial Triple Chamber Cardiac Pacemaker." As seen, this patent discloses a system which provided simultaneous stimulation to both atria through the provision of a Y-connector. That is, a single output from the pulse generator is bifurcated so that stimulation is simultaneously delivered through leads. Typically this bifurcation coupled the leads together in series—one lead stimulating as an anode (preferably that lead stimulating the left atrium within the coronary sinus) and thus requiring a higher threshold, while the other lead would be coupled as cathode (preferably that lead stimulating the right atrium,) and thus requiring a lower threshold. This configuration thus permitted stimulation in either only the right atrium, when the pulse generator was operated in a unipolar mode, or both the left and right atrium, when the pulse generator was operated in a bipolar mode. Of course, when stimulating in both chambers, as discussed above, one lead operated as a cathode while the other operated as an anode. The anode, of course, stimulates less efficiently, and thus requires a high threshold pacing pulse.

SUMMARY OF THE INVENTION

It is thus an object of the present invention to provide a system, adaptor and method to provide medical electrical stimulation to either a single chamber on one side of the heart or two chambers on each side of the heart, for example, either an atrium or both atria of a heart.

It is thus a further object of the present invention to provide a system, adaptor and method for selectively providing medical electrical stimulation to either one or both sides of the heart.

It is thus a further object of the present invention to provide a system, adaptor and method which provides such selective stimulation to either one or both sides of the heart in a cathodic mode.

Briefly, the above and further objects and features of the present invention are realized by providing a system for providing medical electrical stimulation, the system features a pulse generator, the pulse generator generating electrical stimulation pulses of a first amplitude and a second amplitude, first and second elongated leads coupled to the pulse generator, means for directing electrical stimulation pulses of a first amplitude to the first lead and directing electrical stimulation pulses of a second amplitude to the first lead and the second lead, the means for directing electrical stimulation pulses coupled to the pulse generator. In the preferred embodiment the means for directing electrical stimulation pulses is an adaptor featuring a zener diode, the diode being electrically coupled to one of the leads such that electrical stimulation of a first amplitude is not passed through the diode while electrical stimulation of a second amplitude is passed through the diode. Overall the adaptor permits a single channel of stimulation to be split and provided to two areas of the heart merely be adjusting the amplitude of the stimulation pulses.

DETAILED DESCRIPTION OF THE FIGURES

The FIGS. are not necessarily to scale.

DETAILED DESCRIPTION OF THE DRAWINGS

As discussed above, the present invention provides for a simple and reliable means to provide electrical stimulation to either a first area of the heart (such as the right atrium) or to both the first and a second area of the heart (such as the right and left atrium) merely be adjusting the amplitude output of a conventional pacemaker. This is important because it permits a physician to remotely switch between stimulating one atrium of the heart or both atria of the heart. This ability permits the physician to ascertain whether such bi atrial stimulation is beneficial or whether a patient should merely have stimulation pulses delivered to only the one atrium. The present invention may also be used to provide more than bi atrial stimulation, such as also providing four chamber stimulation. The invention, moreover, permits each lead coupled thereto to sense intrinsic activity and communicate it to the pacemaker. In addition, the present invention permits both such leads to be coupled to the pacemaker such that they deliver stimulation in only a cathodic mode, which is a much more efficient mode in which to stimulate. In the preferred embodiment, the present invention is formed as an adaptor which is used to couple two pacing leads to a single output of a pacemaker.

Figure 1A:
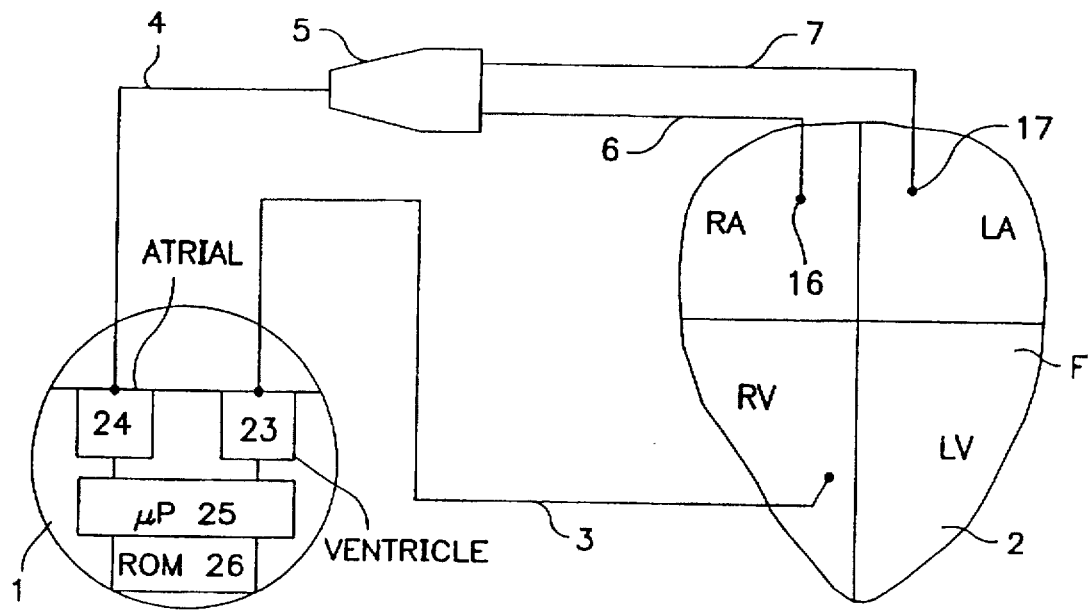
FIG. 1A is a schematic view of the connection of a system according to the present invention coupled to three chambers of the heart.

As seen in FIG. 1A, pacemaker 1 is connected to the heart through a series of leads, 3 and 4. As seen, lead 3 couples the ventricular circuit 23 to the right ventricle. Ventricular circuit 23 provides for the sensing and stimulation of the ventricle, in a conventional manner well known in the art. Lead 3 is preferably a conventional bipolar endocardial lead, as is also well known in the art. Lead 4 couples the atrial circuit 24 to adaptor 5. Atrial circuit 24 provides both sensing and stimulation of the atrium in a conventional manner well known in the art. Lead 4 is preferably constructed along its length as a conventional bipolar endocardial lead. Distal end of lead 4, however, features adaptor 5. Adaptor 5 provides means to switch the stimulation delivered through lead 4 into either or both of leads 6, 7 as described in detail below. As seen, lead 6 is coupled to the right atrium while lead 7 is coupled to the left atrium. Lead 6 may be either a conventional endocardial lead or an epicardial lead and features an electrode 16 at the distal end thereof. Lead 7 may also be a conventional epicardial lead or may also be a lead particularly designed for implantation at or within the coronary sinus. Lead 7 also features an electrode 17. Examples of leads particularly designed for implantation at the coronary sinus may be found in PACE, April 1995, part 11, page 825, Daubert et al. "Experience with a New Coronary Sinus Lead Specifically Designed for Permanent Left Atrial Pacing" as well as that disclosed by Swoyer, U.S. patent application Ser. No. 08/639,458 filed Apr. 29, 1996.

As discussed above, pacemaker 1 may be selected from any of the conventional type pulse generators, such as WI, WIR, DDD, DDDR to name only a few. In the preferred embodiment, however, pacemaker 1 is a DDDR type pacemaker, such as the Medtronic Thera DR available from Medtronic Inc, Minneapolis, Minn., USA. Pacemaker 1 includes ventricular circuits 23 and atrial circuits 24 which may be separately and independently configured to sense cardiac activity in each of the respective chambers and provide electrical stimulation in response thereto. These circuits may be independently configured to also provide either unipolar or bipolar stimulation as is well known in the art. As seen, pacemaker 1 includes a microprocessor 25 and ROM 26 containing software instructions suitable for executing in either the DDD or DDT mode (and perhaps other modes if desired) of pacing. Of course, the present invention is not only limited to the provision of pacing therapy, it may be likewise used for the provision of defibrillation therapy or other types of electrical therapy. The construction and programming of a software routine and fixing of a program in ROM 26 (or any other memory device) to implement the operation of the device are well known in the art.

Figure 1B:
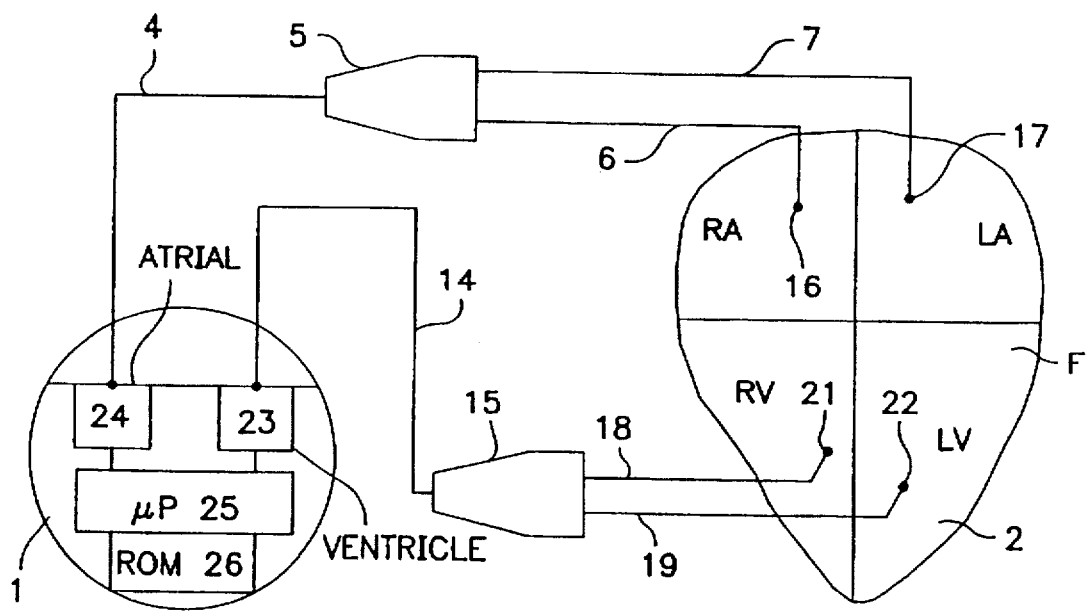
FIG. 1B is a schematic view of the connection of a system according to the present invention coupled to four chambers of the heart.

FIG. 1B depicts an alternative system in which an adaptor 5 of the present invention may be used. As seen the system of FIG. 1B substantially corresponds to that shown in FIG. 1A and thus the same numbers have been used to identify the same components already discussed in regards to FIG. 1A. The system of FIG. 1B, however, differs from that shown in FIG. 1A with the addition of a second adaptor 15 on ventricular lead 14. Second adaptor 15, in turn has two leads 18 and 19 coupled thereto. Lead 14 is preferably constructed along its length as a conventional bipolar endocardial lead. Of course, as mentioned above, the invention may also be used on a unipolar lead. Distal end of lead 14, however, features adaptor 15. Adaptor 15 provides means to switch the stimulation delivered through lead 14 into either or both of leads 18, 19. Adaptor 15 is constructed in a manner similar to adaptor 5 as will be described in detail below. As seen, lead 18 is coupled to the right ventricle while lead 19 is coupled to the left ventricle. Lead 18 may be either a conventional endocardial lead or an epicardial lead and features an electrode 21 at the distal end thereof. Lead 17 may also be a conventional epicardial lead and also features an electrode 22 at the distal end thereof.

Figure 2:
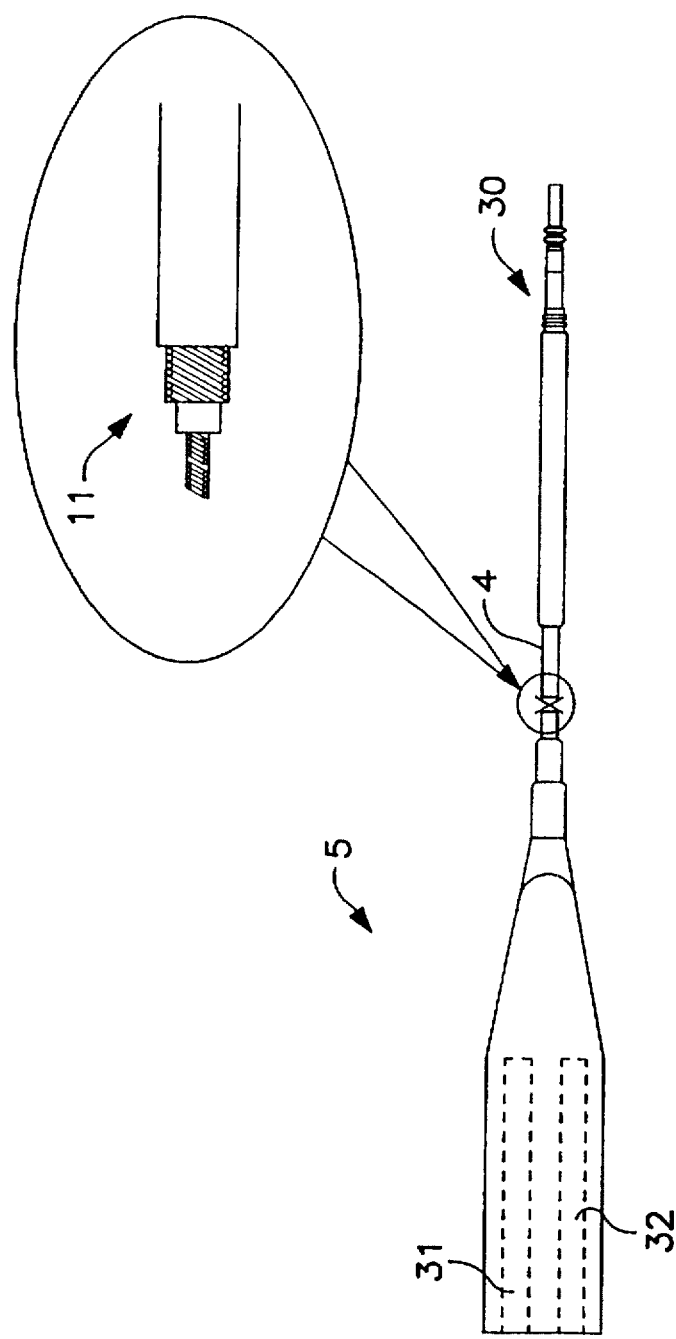
FIG. 2 is a side view of an adaptor used in the system of the present invention.
Figure 3:
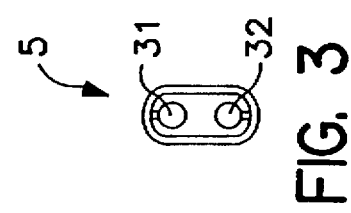
FIG. 3 is an end view of the adaptor shown in FIG. 2.

FIG. 2 is a detailed side view of lead 4 showing adaptor 5. As seen, lead 4 features at its proximal end 30 a connector pin. The connector pin is the standard IS1-bi bipolar connector pin permitting the lead 4 to be coupled into a conventional pacemaker or pulse generator, as discussed above. Lead 4 features a standard bipolar coaxial lead body as is well known in the art, i.e., a inner coiled conductor having an inner insulator sheath within the lumen of an outer coiled conductor, the outer coiled conductor insulated by an outer insulated sheath as shown in the detailed enlargement 11 of FIG. 2. At the distal end of lead 4 is adaptor 5. As seen, adaptor 5 features a pair of connector pin ports 31 and 32. Connector pin ports 31 and 32 provide for the insertion of the connector pins of medical electrical leads into the adaptor, as will be described below. FIG. 3 shows an end view of lead 4 and in particular the layout for the connector pin ports 31, 32.

Figure 4:
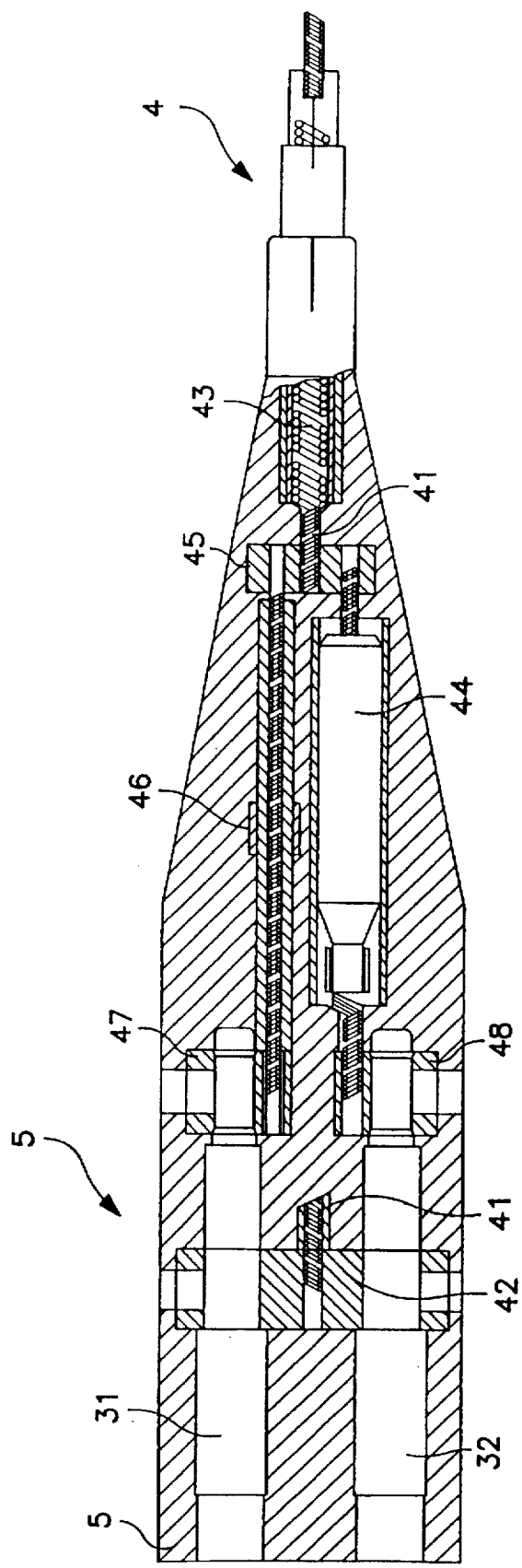
FIG. 4 is a sectional side view of an adaptor used in the system of the present invention.

FIG. 4 shows a detailed cutaway view of adaptor 5 of lead 4. As seen, inner conductor 41 is coupled to contact ring 42. As seen, contact ring 42 has two holes which each correspond with ports 31, 32 to thereby provide an electrical coupling to any lead inserted therein. Likewise, outer conductor 43 is electrically coupled to coil guide 45. Coil guide 45 electrically couples outer conductor 43 to both electronic capsule 44 and coil 46. Coil 46, in turn, is electrically coupled to first connector port 47. Electronic capsule 44, in turn, electrically couples conductor 43 with second connector port contact 48. As described below, electronic capsule 44 provides for selective activation or electronic coupling of second connector port 32 with the conductor 43. Adaptor 5 is seated within a hermetically sealed housing, as is common among implantable devices.

Figure 5:
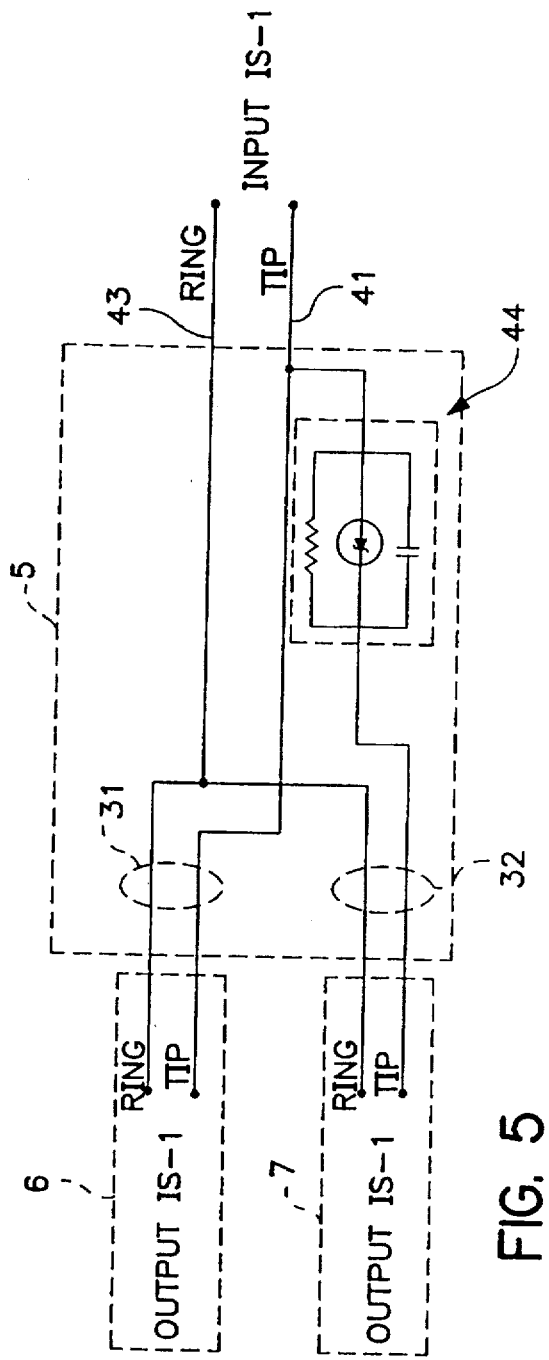
FIG. 5 is a schematic view of the system according to the present invention.

FIG. 5 shows a schematic of adaptor 5. As seen, adaptor 5 couples outer conductor 43 to both ring conductors of leads 6 and 7. Adaptor 5 further couples inner conductor 41 or tip to the tip of lead 6 as well as the tip of lead 7 through electronic module 44. As described above, adaptor 5 and in particular electronic module 44 enables the stimulation to be controlled via one or both leads. In particular, electronic module provides for the switching from one channel stimulation along lead 6 to two channel stimulation along lead 6 and 7 through the mere variation of output amplitude. That is, the increase of output amplitude by pacemaker 1 allows either one or two chamber stimulation due to the unique characteristics of electronic module 44. In particular, electronic module 44 only provides for the conduction of electronic stimulus therethrough if a certain amplitude of stimulation is reached. In the preferred embodiment, the preferred amplitude of stimulation is 2.5 volts.

Figure 6:
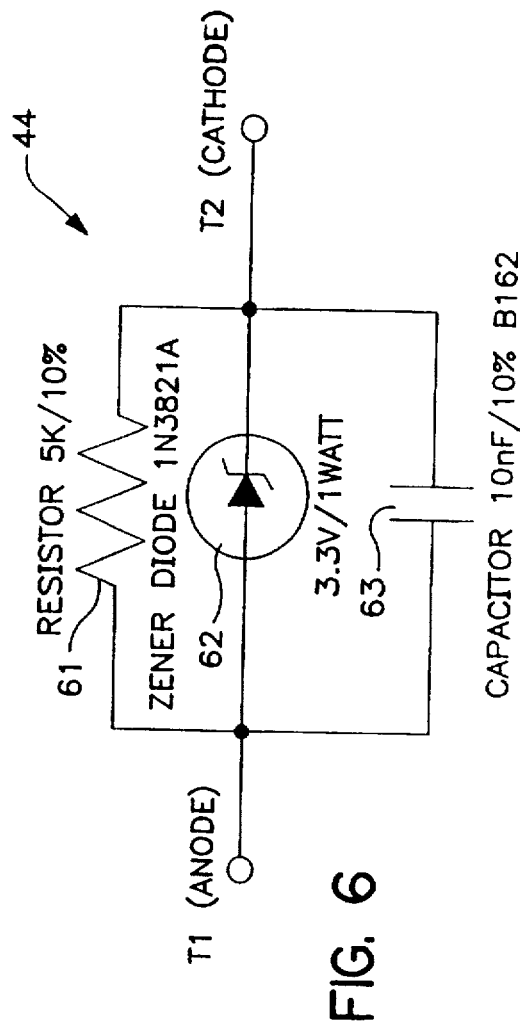
FIG. 6 is a schematic view of the electronic capsule used in the system of the present invention.

FIG. 6 is a detailed schematic view of electronic module 44. As seen, electronic module 44 comprises a resistor 61, zener diode 62 and capacitor 63 all coupled in parallel. Zener diode 62 preferably has a forward voltage of 0.7±0.1 V at IF=10 mA. In the preferred embodiment, resistor 61 has a value of 5 k Ohms while capacitor 63 has a capacity of 10 nF. Resistor 61 and capacitor 63 are provided to permit sensing along lead 7. Thus the adaptor of the present invention allows for sensing through both the lead 7 as well as the lead 6.

Figure 7:
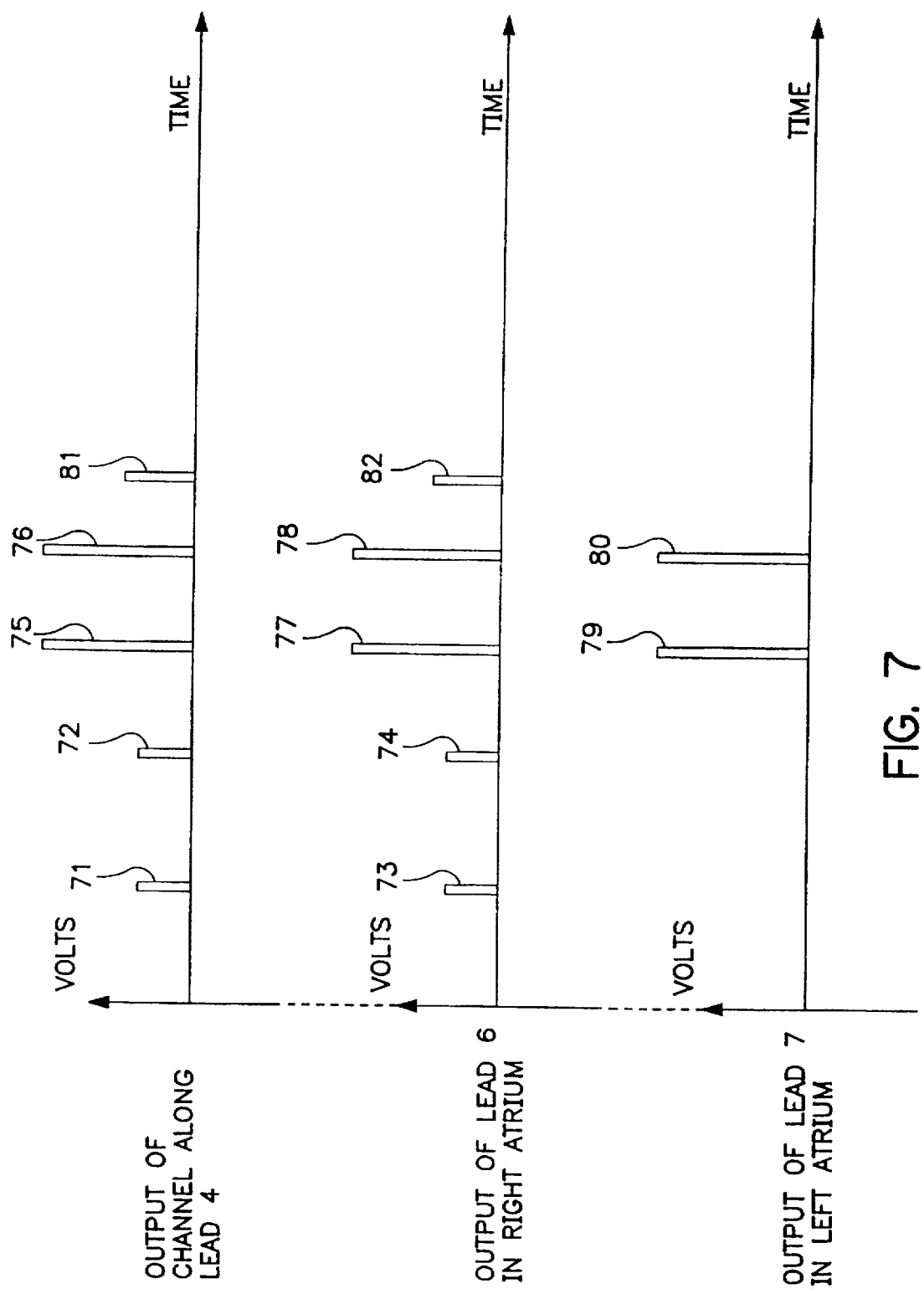
FIG. 7 depicts the pulses emitted by the pulse generator and directed to each of the leads.

FIG. 7 is an example of the operation of the present invention. As seen, pacing pulses 71 and 72 through the atrial channel long lead 4 are output as pacing pulses 73 and 74 through lead 6 in right atrium. When the output of atrial channel along lead 4 is increased in amplitude, as seen, with pacing pulses 75 and 76, then through the unique design of adaptor 5, these pacing pulses are experienced as both outputs along lead 6 and lead 7, shown here as output pulses 77 and 78 as well a 79 and 80 respectively. Finally, when the amplitude of output pulse along atrial channel of lead 4 is again reduced to its first level, as exemplified by output pulse 81, then the electronic capsule 44 of adaptor 5 blocks the output along lead 7 and only output pulse 82 along lead 6 in the right atrium is produced.

While the embodiment of the present invention as described in particular detail in regard to cardiac stimulation and in particular to cardiac pacing, the present invention may also be practiced using other medical electrical technologies where the aforementioned characteristics are desirable, including neurological and muscle stimulation applications, as well as other forms of electrically stimulating other body tissues or organs. It should be understood variations and modifications of the present invention may be made while still being within the scope of any of the following claims. These variations may include using the present invention to direct various electrical stimulation therapies to various points within the body, such a defibrillation, muscle stimulation or neurological therapies. Such variations and modifications may also include substituting elements or components which perform substantially the same function in substantially the same way to achieve substantially the same results for those described herein.

What is claimed is:

1. A system to provide medical electrical stimulation to a patient's heart comprising:

a pulse generator, the pulse generator generating electrical pacing stimulation pulses of a first pacing amplitude and a second pacing amplitude;

a first lead coupled to the pulse generator, the first lead having a first lead body, the first lead body having a first distal end, a first electrode located at the first distal end;

a second lead, the second lead having an second lead body, the second lead body having a second distal end, a second electrode located at the second distal end; and means for directing electrical pacing stimulation pulses of a first pacing amplitude through the first lead to the first electrode and directing electrical pacing stimulation pulses of a second pacing amplitude through the second lead to the first electrode and through the second lead to the second electrode, the means for directing electrical pacing stimulation pulses coupled to the pulse generator wherein the means for directing electrical pacing stimulation pulses of a first pacing amplitude to the first electrode and directing electrical pacing stimulation pulses of a second pacing amplitude to the first electrode and the second electrode comprises a zener diode electrically coupling the second lead to the pulse generator; and means for sensing through the second electrode, the means for sensing comprising a capacitor and a resistor coupled to the second lead body in parallel to the zener diode wherein electrical signals present at the second electrode may be conducted through the second lead body to the pulse generator.

2. A system to provide medical electrical stimulation to a patient's heart according to claim 1 wherein the zener diode has a threshold of no more than the second amplitude.

3. A system to provide medical electrical stimulation to a patient's heart according to claim 1 wherein the capacitor has a capacitance of 12 nF and the resistor has a resistance of 5 K Ohms.

4. A system to provide medical electrical stimulation to a patient's heart according to claim 1 wherein the means for directing electrical pacing stimulation pulses of a first pacing amplitude to the first electrode and directing electrical pacing stimulation pulses of a second pacing amplitude to the first electrode and the second electrode is an adaptor, the adaptor comprising:

a pulse generator connector coupled to the pulse generator;

an adaptor lead body coupled to the pulse generator connector; and an adaptor housing coupled to the first lead body, the adaptor housing having a first lead port into which the first lead is coupled and a second lead port into which the second lead is coupled, the adaptor housing having a zener diode electrically coupling the second lead to the pulse generator.

5. An adaptor for directing electrical stimulation pulse from a first lead to both the first lead and a second lead, the adaptor comprising:

means for coupling to a pulse generator;

means for coupling with a first lead and a second lead; and means for directing pacing stimulation pulses of a first pacing energy level to the first lead and directing pacing stimulation pulses of a second pacing level to the first lead and the second lead wherein the means for directing electrical pacing stimulation pulses of a first pacing amplitude to the first lead and directing electrical pacing stimulation pulses of a second pacing amplitude to the first lead and the second lead comprises a zener diode electrically coupling the second lead to the pulse generator; and means for sensing through the second electrode, the means for sensing comprising a capacitor and a resistor coupled to the second lead body in parallel to the zener diode wherein electrical signals present at the second electrode may be conducted through the second lead body to the pulse generator.

6. The adaptor according to claim 5 further comprising an adaptor lead body, the adaptor lead body having a first end and a second end, the first end of the adaptor lead body coupled to the means for coupling to a pulse generator, the second end of the adaptor lead body coupled to the means for coupling with a first lead and a second lead.

7. A method of electrically stimulating either a first chamber of the heart or the first and the second chamber of the heart comprising:

coupling a first lead to the first chamber the first lead having a first electrode;

coupling a second lead to the second chamber, the second lead having a second electrode;

providing means for directing electrical pacing stimulation pulses of a first pacing amplitude to the first electrode and directing electrical pacing stimulation pulses of a second pacing amplitude to the first electrode and the second electrode;

coupling the first lead and the second lead to the means for directing electrical stimulation pacing pulses;

providing a pulse generator which emits electrical stimulation pacing pulses of a first pacing amplitude and a second pacing amplitude;

coupling the means for directing electrical stimulation pacing pulses to the pulse generator;

emitting electrical stimulation pacing pulses of the first pacing amplitude from the pulse generator;

directing the electrical stimulation pacing pulses of the first pacing amplitude from the pulse generator to the first electrode;

emitting electrical stimulation pacing pulses of the second pacing amplitude from the pulse generator; and directing the electrical stimulation pacing pulses of the second pacing amplitude from the pulse generator to the first electrode and the second electrode.

\* \* \* \* \*